United States Patent [19]

Johnson et al.

[11] Patent Number: 4,911,159
[45] Date of Patent: Mar. 27, 1990

[54] ELECTROSURGICAL INSTRUMENT WITH ELECTRICAL CONTACTS BETWEEN THE PROBE AND THE PROBE HOLDER

[76] Inventors: Jeffrey W. Johnson; Gerald W. Johnson, both of 17070 Red Oak, Suite 301, Houston, Tex. 77090

[21] Appl. No.: 274,497

[22] Filed: Nov. 21, 1988

[51] Int. Cl.[4] ............................................. A61B 17/36
[52] U.S. Cl. ........................................ 606/37; 606/39; 606/40; 606/42; 606/45; 606/49
[58] Field of Search ........................ 128/303.13–303.17

[56] References Cited

U.S. PATENT DOCUMENTS

| | | | |
|---|---|---|---|
| 4,032,738 | 6/1977 | Esty et al. | 128/303.13 |
| 4,034,761 | 7/1977 | Prater et al. | 128/303.17 |
| 4,427,006 | 1/1984 | Nottle | 128/303.17 |
| 4,655,215 | 4/1987 | Pike | 128/303.17 |
| 4,719,914 | 1/1988 | Johnson | 128/303.14 |

Primary Examiner—Max Hindenburg
Attorney, Agent, or Firm—Neal J. Mosely

[57] ABSTRACT

An electrosurgical apparatus comprises an electrosurgical generator for producing cutting and coagulation signals and has either pedal operated or hand operated switches for switching on and off and between cutting and coagulation signals. A cutting and coagulation probe is energized by the generator and has a handle portion and a probe element. An on/off switch controls energization of the probe element. A switch is operated to switch the probe element between the cutting current and coagulation current. A holder member removably supports the probe element and has an electric socket therein. The probe element is removably supported in the holder member and has an electric connector cooperable with the holder member socket to complete an electric connection to the probe element. An electric connector connects the probe element to the electrosurgical generator circuit. The on/off switch may be in the holder element or in a pedal operated switch. The switch controlling application of cutting current and coagulation current may also be either in the holder element or in a pedal operated switch. The probe may be a hollow tubular member having an opening at one end adapted for connection by hollow tubing to a source of vacuum and having an arrangement for selective application of vacuum at the cutting end thereof.

30 Claims, 2 Drawing Sheets

ELECTROSURGICAL INSTRUMENT WITH ELECTRICAL CONTACTS BETWEEN THE PROBE AND THE PROBE HOLDER

BACKGROUND OF THE INVENTION

1. Field of the Invention

This invention relates generally to electrosurgical instruments and more particularly to electrosurgical instruments with replaceable blades.

2. Brief Description of the Prior Art

Electrosurgical instruments are known for use in a variety of surgical procedures.

The electrosurgical generators and associated blades and instruments have been manufactured and sold by Valleylab, Inc. of Boulder, Colo. for many years. Other electrosurgical generators and associated blades and instruments have been manufactured and sold by other companies such as Sybron Corporation, of Rochester, N.Y., and The Birtcher Corporation of Los Angeles, Calif.

A number of U.S. patents show representative electrosurgical apparatus with which the present invention may be used. Newton U.S. Pat. No. 3,897,788, assigned to Valleylab, Inc., discloses a transformer coupled power transmitting and isolated switching circuit for use in an electrosurgical apparatus.

Oosten U.S. Pat. No. 4,318,409, assigned to Medical Research Associated Ltd., discloses an electrosurgical generator which may be switched between mono-polar an bipolar operation, and between cutting and coagulating functions.

Anderson U.S. Pat. No. 3,699,967, assigned to Valleylab, Inc., discloses an electrosurgical generator which produces cutting and coagulating currents and may be switched between cutting and coagulating outputs.

Morrison U.S. Pat. No. 4,060,088, assigned to Valleylab, Inc., discloses an electrosurgical apparatus with a cutting blade or needle arranged to be blanketed by inert gas.

Newton U.S. Pat. No. 3,801,800, assigned to Valleylab, Inc., discloses an isolating switching circuit for an electrosurgical generator.

Newton U.S. Pat. No. 3,897,787, assigned to Valleylab, Inc., discloses a transformer coupled power transmitting and isolated switching circuit for an electrosurgical generator.

Newton U.S. Pat. No. 3,963,030, assigned to Valleylab, Inc., discloses an electrosurgical generator for producing a coagulating current for use in a surgical procedure.

Harris U.S. Pat. No. 4,188,927, assigned to Valleylab, Inc., discloses a multiple source electrosurgical generator which may be switched between mono-polar and bipolar operation, and between cutting and coagulating functions.

Harris et al U.S. Pat. No. 4,658,819, assigned to Valleylab, Inc., discloses an electrosurgical generator with a circuit for decreasing output power with increasing patient impedance.

Judson U.S. Pat. No. 3,885,569, assigned to The Birtcher Corporation, discloses an electrosurgical generator which may be switched between cutting an coagulating signals and mixed signals by a mode control circuit which is responsive to the operation of selector switches and/or manually operated actuators.

Archibald U.S. Pat. No. 4,030,501, assigned to Minn. Mining and Manufacturing Company, discloses an electrosurgical generator which may be switched between cutting and coagulating signals and mixed signals by a transistorized switching circuit. Sittner U.S. Pat. No. 4,038,984, assigned to Electro - Medical Systems, Inc., discloses an electrosurgical generator which may be switched between cutting and coagulating signals.

Meinke et al U.S. Pat. No. 4,209,018 discloses an electrosurgical apparatus having means to control the arc generated during surgery to minimize formation of albumen during coagulating operation.

Woltosz U.S. Pat. No. 4,211,230, assigned to Sybron Corporation, discloses an electrosurgical apparatus with pulse control to allow sufficient cooling time to prevent cell volatilization.

Manes U.S. Pat. No. 4,574,801, assigned to Aspen Laboratories Inc., discloses an electrosurgical apparatus with pulse control.

A number of other patents disclose electrosurgical apparatus showing details of the cutting and coagulation probes used in surgery.

Seeliger U.S. Pat. No. 3,058,470, assigned to Siemans-Reiniger-Werke AG., discloses an electrosurgical apparatus with a cutting and coagulation electrode or probe controlled by a foot switch or a switch in the probe handle.

Estes U.S. Pat. No. 3,601,126, assigned to Electro Medical Systems, Inc., discloses an electrosurgical apparatus with a cutting and coagulation electrode or probe controlled by a pair of remote switches.

Bross U.S. Pat. No. 4,211,230, assigned to Sybron Corporation, discloses an electrosurgical apparatus with a cutting and coagulation electrode or probe.

Childs et al U.S. Pat. No. 4,334,539, assigned to Cimmaron Instruments, Inc., discloses an electrosurgical apparatus with a cutting and coagulation electrode or probe controlled by switches in the probe handle.

Perkins U.S. Pat. No. 4,071,020 discloses an electrosurgical apparatus with a cutting and coagulation electrode or probe controlled by switches in the probe handle.

Garito U.S. Pat. No. 4,463,759 discloses a universal finger/foot switch adapter for electrosurgical apparatus.

The present invention is distinguished over the prior art in general, and these patents in particular by providing an electrosurgical apparatus which comprises an electrosurgical generator for producing cutting and coagulation signals and has either pedal operated or hand operated switches for switching on and off and between cutting and coagulation signals. A cutting and coagulation probe is energized by the generator and has a handle portion and a probe element. An on/off switch controls energization of the probe element. A switch is operated to switch the probe element between the cutting current and coagulation current. A holder member removably supports the probe element and has an electric socket therein. The probe element is removably supported in the holder member and has an electric connector cooperable with the holder member socket to complete an electric connection to the probe element. An electric connector connects the probe element to the electrosurgical generator circuit. The on/off switch may be in the holder element or in a pedal operated switch. The switch controlling application of cutting current and coagulation current may also be either in the holder element or in a pedal operated switch. The probe may be a hollow tubular member having an opening at one end adapted for connection by hollow tubing to a source of vacuum and having an arrangement for selective application of vacuum at the cutting end thereof.

SUMMARY OF THE INVENTION

It is therefore an object of the present invention to provide a new and improved electrosurgical apparatus having replaceable and disposable electrosurgical instruments.

It is another object of this invention is to provide a new and improved electrosurgical apparatus with a pedal operated switch for switching between cutting and coagulation signals and having replaceable and disposable electrosurgical instruments.

Another object of this invention is to provide a new and improved electrosurgical apparatus with a hand held switch for switching between cutting and coagulation signals and having replaceable and disposable electrosurgical instruments.

Another object of this invention is to provide a new and improved electrosurgical apparatus with a pedal operated switch for switching between cutting and coagulation signals and having an electrically connected holder for replaceable and disposable hand held electrosurgical instruments.

Still another object of this invention is to provide a new and improved electrosurgical apparatus with an electrically connected holder held by hand with a switch for switching between cutting and coagulation signals applied to replaceable and disposable electrosurgical instruments.

Still another object of this invention is to provide a new and improved electrosurgical apparatus with a switch for switching between cutting and coagulation signals and having an electrically connected holder having an electrical connector receiving a replaceable and disposable hand held electrosurgical instrument having an electrical connector cooperable therewith.

A further object of this invention is to provide a new and improved electrosurgical apparatus with an electrically connected holder having a switch for switching between cutting and coagulation signals and an electrical connector receiving a replaceable and disposable hand held electrosurgical instrument having an electrical connector cooperable therewith.

A further object of this invention is to provide a new and improved electrosurgical apparatus with a pedal operated switch for switching between cutting and conagulation signals and having an electrically connected holder having an off/on switch and an electrical connector receiving a replaceable and disposable hand held electrosurgical instrument having an electrical connector cooperable therewith.

Other objects of the invention will become apparent from time to time throughout the specification and claims as hereinafter related.

The above noted objects and other objects of the invention are accomplished by a novel electrosurgical apparatus which comprises an electrosurgical generator for producing cutting and coagulation signals and has either pedal operated or hand operated switches for switching on and off and between cutting and coagulation signals. A cutting and coagulation probe is energized by the generator and has a handle portion and a probe element. An on/off switch controls energization of the probe element. A switch is operated to switch the probe element between the cutting current and coagulation current. A holder member removably supports the probe element and has an electric socket therein. The probe element is removably supported in the holder member and has an electric connector cooperable with the holder member socket to complete an electric connection to the probe element. An electic connector connects to probe element to the electrosurgical generator circuit. The on/off switch may be in the holder element or in a pedal operated switch. The switch controlling application of cutting current and coagulation current may also be either in the holder element or in a pedal operated switch. The probe may be a hollow tubular member having an opening at one end adapted for connection by hollow tubing to a source of vacuum and having an arrangement for selective application of vacuum at the cutting end thereof.

DESCRIPTION OF A PRIOR ART EMBODIMENT

Figure 1:
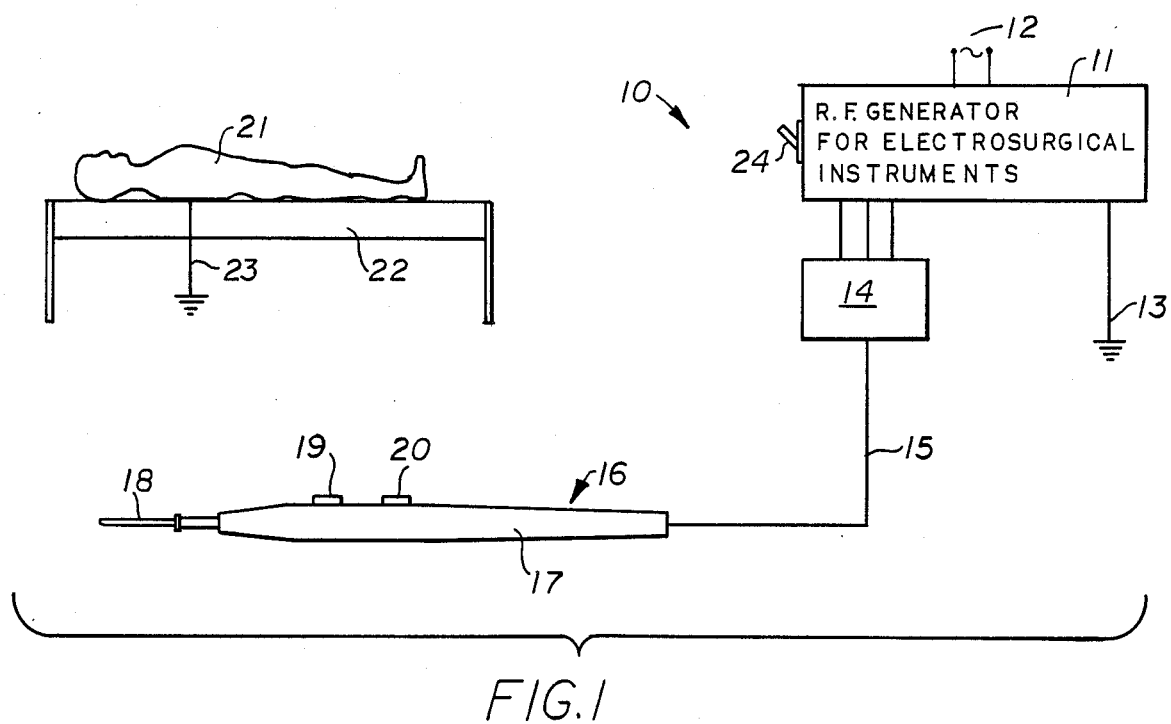
FIG. 1 is a schematic view of a prior-art electrosurgical apparatus having a hand held electrosurgical probe with switches for switching between a cutting and a coagulation signal.

Referring to the drawings by numerals of reference, and morre particularly to FIG. 1, there is shown a schematic view of a prior art electrosurgical apparatus 10 comprising a RF generator 11 and associated circuit for producing high frequency currents for use in surgery, particularly in microsurgery. The apparatus may utilize the generator and associated circuits in any of the prior art patents referenced above and produces one frequency for use in cutting and another frequency for use in coagulation or cauterization. Generator 11 is connected to a suitable A.C. power source 12 and is connected to ground 13.

Generator 11 is connected by a multiple terminal plug 14 and electric lead 15 to supply both cutting and coagulation frequencies to an electrosurgical probe 16. Probe 16 has a handle portion 17 which is a hollow tube receiving electric lead 15 at one end and a cutting blade 18 at the other end. The term cutting blade, as used herein, includes both cutting blades having a narrow, flat edge, and pointed needles. Cutting blade 18 is connected to electric lead 15 through a pair of switches 19 and 20 which connect cutting and coagulating frequencies, respectively, from electric lead 15 and generator 11.

The apparatus is used in surgery on a patient 21 supported on an operating table 22 and connected to ground 23 to complete the circuit back to generator 11. In use, the generator is turned on by an on/off switch 24 which energizes generator 11 and supplies both cutting and coagulating frequencies through electric lead 15 to probe 16. The surgeon holds probe 16 by handle 17 and switches between cutting and coagulating frequencies as needed. The probes 16 are disposed of after use since the blade 18 cannot be reused on other patients. This makes electrosurgery more expensive because of the cost of continual replacement of the electrosurgical probes 16 which contain part of the circuit and the switches 19 and 20.

DESCRIPTION OF ANOTHER PRIOR ART EMBODIMENT

Figure 2:
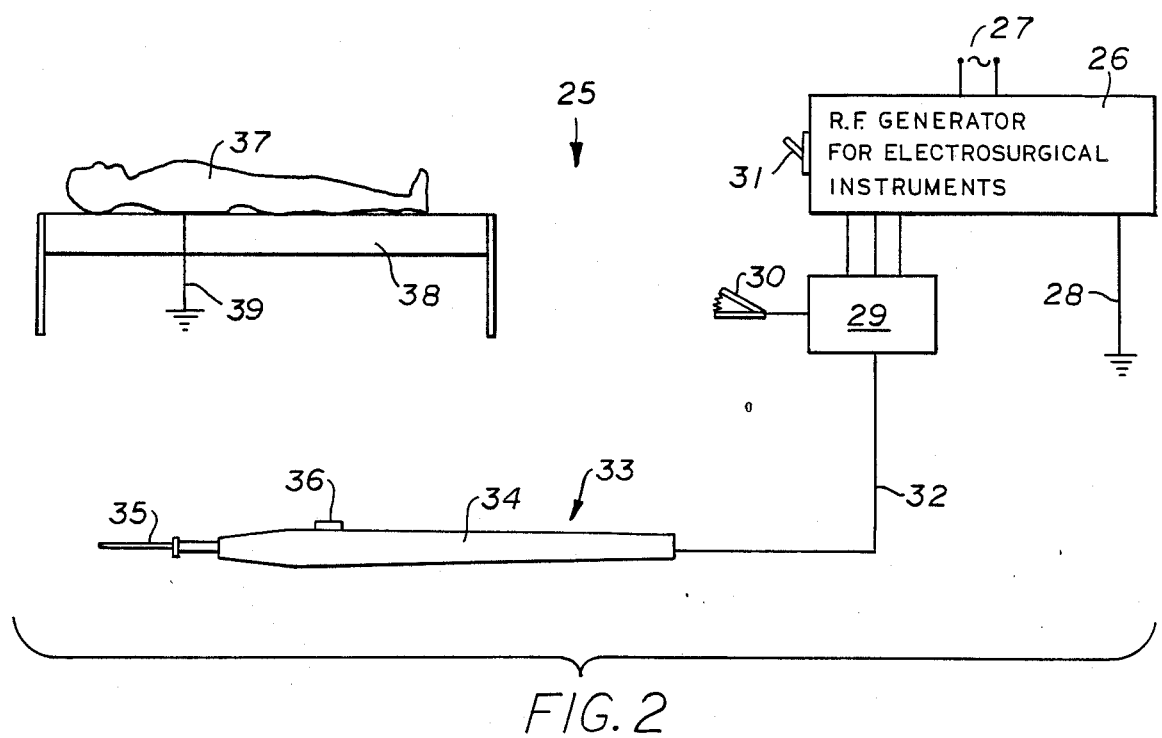
FIG. 2 is a schematic view of a prior-art electrosurgical apparatus having a hand held electrosurgical probe with an off/on switch and having a pedal operated switch for switching between a cutting and a coagulation signal.

Referring to the drawings by numerals of reference, and more particularly to FIG. 2, there is shown a schematic view of another prior art electrosurgical apparatus 25 comprising a RF generator 26 and associated circuit for producing high frequency currents for use in surgery, particularly in microsurgery. The apparatus may utilize the generator and associated circuits in any of the prior art patents referenced above and produces one freqeuncy for use in cutting and another freqency for use in coagultion or cauterization. Generator 26 is connected to a suitable A.C. power source 27 and is connected to ground 28.

Generator 26 is connected by a multiple terminal plug 29 to a pedal switch 30 which switches between cutting and coagulating frequencies. Generator is turned on by an on/off switch 31. Electric lead 32 connects either cutting or coagulation frequencies to an electrosurgical probe 33 according to the state of operation of pedal switch 30. Probe 33 has a handle portion 34 which is a hollow tube receiving electric lead 32 at one end and a cutting blade 35 at the other end. The term cutting blade, as used herein, includes both cutting blades having a narrow, flat edge, and pointed needles. Cutting blade 35 is connected to electric lead 32 through a switch 36 which is an on/off switch for applying cutting and coagulating frequencies, respectively, from electric lead 32 and generator 26.

The apparatus is used in surgery on a patient 37 supported on an operating table 38 and connected to ground 39 to complete the circuit back to generator 26. In use, the generator 26 is turned on by an on/off switch 31 which energizes generator 26 and supplies both cutting and coagulating frequencies to pedal switch 30 and thence through electric lead 32 to probe 33. The surgeon holds probe 33 by handle 34 and switches cutting and coagulating frequencies on by means of switch 36. The probes 33 are disposed of after use since the blade 35 cannot be reused on other patients. This makes electrosurgery more expensive because of the cost of continual replacement of the electrosurgical probes 33 which contain part of the circuit and the switch 36.

DESCRIPTION OF A PREFERRED EMBODIMENT OF THE INVENTION

Figure 3:
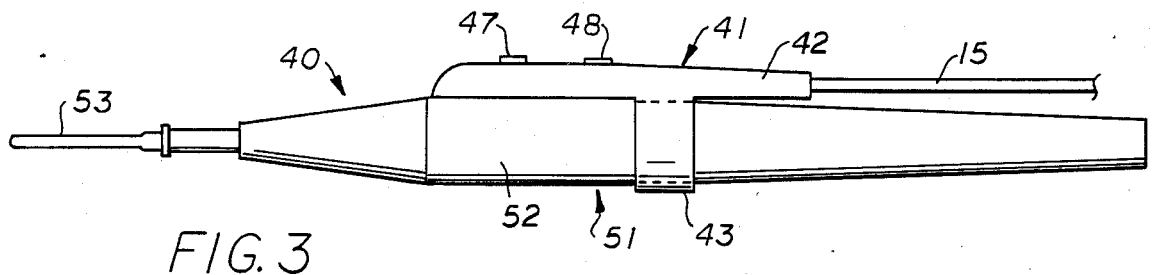
FIG. 3 is a view in side elevation of a new and improved electrically connected holder for an electrosurgical apparatus having a switch for switching between cutting and coagulation signals and an electrical connector receiving a replaceable and disposable hand held electrosurgical probe having an electrical connector cooperable therewith.
Figure 4:
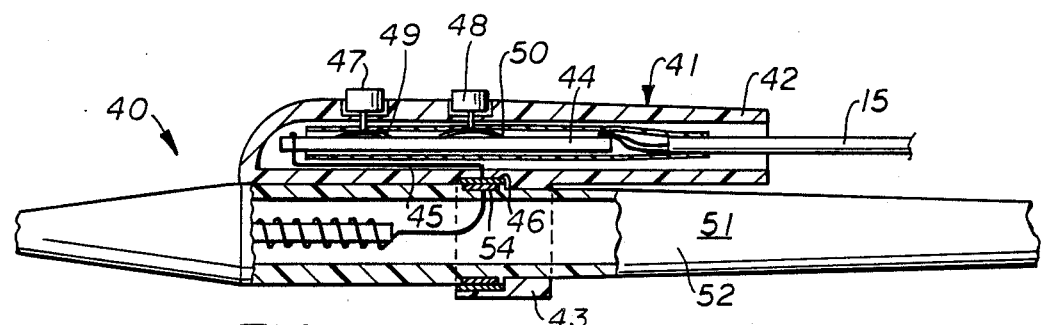
FIG. 4 is a longitudinal cross section of the holder and electrosurgical probe shown in FIG. 3.

Referring to FIGS. 3 and 4, there is shown a probe assembly 40 for use in the electrosurgical apparatus of the type shown in FIG. 1. Probe assembly 40 has a holder 41 with a hollow handle portion 42 which receives electric lead 15 at one end and has a supporting sleeve 43 at its mid-portion. Electric lead 15, which conducts both cutting and coagulation frequencies in separate wires, is connected to a circuit board 44 connected at 45 to an electric contact 46 in supporting sleeve 43. Switch buttons 47 and 48 operate contacts 49 and 50 to connect either the cutting frequency or the coagulation frequency from electric lead 15 (and high frequency generator11) to contact 46. Sleeve 43 and contact 46 therefore constitute an electric socket for connection to a disposable electrosurgical probe 51.

Electrosurgical probe 51 is functionally the same as the probe 16 in the prior art embodiment of FIG. 1 without the switches 19 and 20. Probe 51 has a hollow tube 52 with a cutting blade 53 at the outer or distal end which is connected electrically to a metal contact 54 in the wall thereof. Hollow tube 52 fits in supporting sleeve 43 with its metal contact 54 making connection with contact 46. Probe 51 is therefore removably supported in sleeve 43 of holder 41 and may be disposed of without throwing away the control switches 47 and 48. The term cutting blade, as used herein, includes both cutting blades having a narrow, flat edge, and pointed needles. Cutting blade 53 is connected to electric lead 15 through contacts 54 and 46, and switches 47 and 48 which connect cutting and coagulating frequencies, respectively, from electric lead 15 and generator 11.

The apparatus is used in surgery on a patient 21 supported on an operating table 22 and connected to ground 23 to complete the circuit back to generator 11. In use, the generator is turned on by an on/off switch 24 which energizes generator 11 and supplies both cutting and coagulating frequencies through electric lead 15 to disposable electrosurgical probe 51. The surgeon holds probe 51 by holder 41 and switches between cutting and coagulating frequencies as needed by means of switches 47 and 48 in the holder. The probes 51 are disposed of after use since the blade 53 cannot be reused on other patients. This makes electrosurgery more economical because of the cost of continual replacement of the electrosurgical probes 51 is reduced by not having to replace the portion of the circuit and the switches 47 and 48 which are in the holder 41.

DESCRIPTION OF ANOTHER PREFERRED EMBODIMENT

Figure 5:
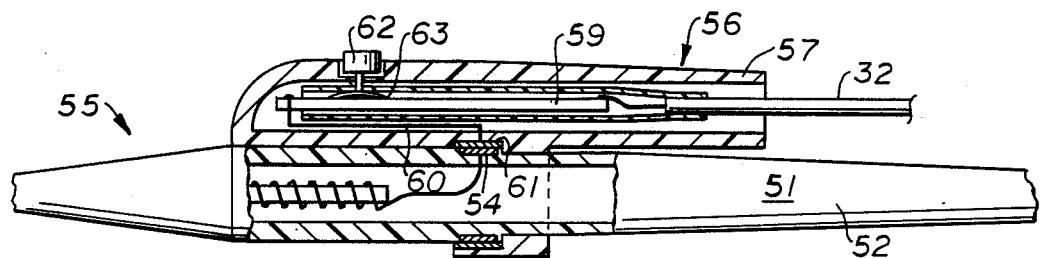
FIG. 5 is a longitudinal cross section of a new and improved electrically connected holder, for use with an electrosurgical apparatus having a pedal operated switch for switching between cutting and coagulation signals, having an off/on switch and an electrical connector receiving a replaceable and disposable hand held electrosurgical probe having an electrical connector cooperable therewith.

Referring to FIG. 5, there is shown a probe assembly 55 for use in the electrosurgical apparatus of the type shown in FIG. 2. Probe assembly 55 has a holder 56 with a hollow handle portion 57 which receives electric lead 32 at one end and has a supporting sleeve 58 at its mid-portion. Electric lead 32, which conducts both cutting and coagulation frequencies in a single lead, is connected to a circuit board 59 connected at 60 to an electric contact 61 in supporting sleeve 58. Switch button 62 operates contact 63 to connect either the cutting frequency or the coagulation frequency (as determined by pedal switch 30) from electric lead 32 (and high frequency generator 26) to contact 61. Sleeve 58 and contact 61 therefore constitute an electric socket for connection to a disposable electrosurgical probe 51.

Electrosurgical probe 51 is functionally the same as the probe 16 in the prior art embodiment of FIG. 1 and the embodiment of FIGS. 3 and 4, without the switches 19 and 20. Probe 51 has a hollow tube 52 with a cutting blade 53 at the outer or distal end which is connected electrically to a metal contact 54 in the wall thereof. Hollow tube 52 fits in supporting sleeve 58 with its metal contact 54 making connection with contact 61. Probe 51 is therefore removably supported in sleeve 58 of holder 56 and may be disposed of without throwing away the control switches 47 and 48. The term cutting blade, as used herein, includes both cutting blades havng a narrow, flat edge, and pointed needles. Cutting blade 53 is connected to electric lead 32 through contacts 54 and 61, and switch 62 which connects cutting and coagulating frequencies, respectively, (according to the state of operation of pedal switch 30) from electric lead 32 and generator 26.

The apparatus is used in surgery on a patient 37 supported on an operating table 38 and connected to ground 39 to complete the circuit back to generator 26. In use, the generator is turned on by an on/off switch 31 which energizes generator 26 and supplies both cutting and coagulating frequencies through pedal switch 30 and electric lead 32 to disposable electrosurgical probe 51. The surgeon holds probe 51 by holder 56 and switches between cutting and coagulating frequencies as needed by means of pedal switch 39 and applies cutting or coagulating frequencies to blade 53 by switch 62 in the holder. The probes 51 are disposed of after use since the blade 53 cannot be reused on other patients. This makes electrosurgery more economical becuase of the cost of continual replacement of the electrosurgical probes 51 is reduced by not having to replace the portion of the circuit and the switch 63 which is in the holder 56.

DESCRIPTION OF ANOTHER PREFERRED EMBODIMENT

Figure 6:
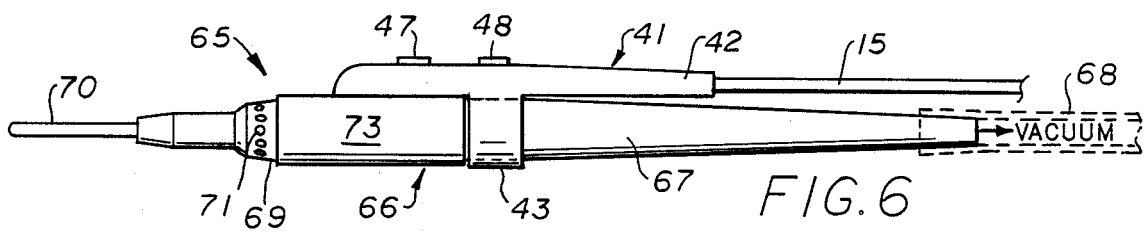
FIG. 6 is a view in side elevation of the electrically connected holder installed on a disposable hand held electrosurgical probe which provides vacuum in cauterizing applications.
Figure 7:
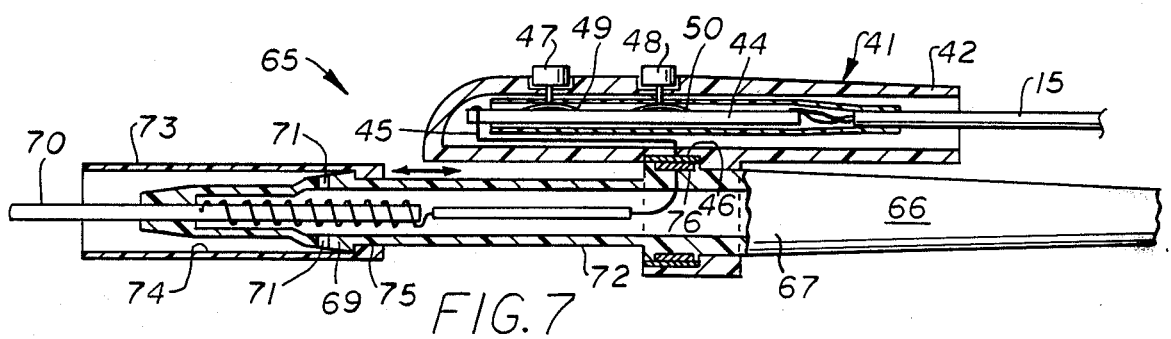
FIG. 7 is a longitudinal cross section of the holder and electrosurgical probe shown in FIG. 6.

Referring to FIGS. 6 and 7, there is shown another electrosurgical instrument or probe assembly 65 which provides vacuum during cauterizing procedures. The electrical connector holder used in this can either be the same as the two switch version shown in FIGS. 3 and 4 or the single switch/foot pedal version shown in FIG. 5. For purposes of illustration, the holder used in the example of FIGS. 6 and 7 is the same as the holder 41 (FIGS. 3 and 4) and has the same reference numerals, however, to avoid repetition, their description will not be repeated in detail to avoid repetition.

Holder 41 has the previously described hollow handle portion 42 which receives electric lead 15 at one end and has a supporting sleeve 43 at its mid-portion. Switch buttons 47 and 48 operate contacts 49 and 50 to connect either the cutting frequency or the coagulation frequency from electric lead 15 (and high frequency generator 11) to contact 46. Sleeve 43 and contact 46 therefore constitute an electric socket for connection to the electrosurgical probe 66.

Electrosurgical probe 66 has a hollow tubular body 67 open at one for connection by a hollow tubing 68 to a source of vacuum and the opposite end includes a tapered hollow nose portion 69 which may be integral with the tubular member or a separate piece. An electrocauterizing blade 70 is secured in and has one end extending outward from the end of the nose portion 69 and the other end positioned inside the tubular body 67. The nose portion 69 has a plurality of openings 71 adjacent to the tapered surface thereof for withdrawing smoke from a surgical area being cut and cauterized by means of vacuum connected to the open end of the tubular body 67. The body 67 has a reduced outside diameter portion 72 along its length.

An imperforate tubular sleeve member 73 having a large inside diameter 74 and smaller inside diameter 75 at one end is slidably supported for longitudinal movement on the reduced diameter portion 72 of the body 67 between a retracted and an extended position. The larger inside diameter 74 of the sleeve 73 and tapered surface of the nose portion 69 cooperate when the sleeve member is moved to an extended position to provide a passage for directing flow of smoke and gases from a coagulation site through the nose portion openings 71 and the tubular body 67 when vacuum is applied thereto. Thus, selective control of the application of vacuum through the nose portion openings 71 is provided by the sleeve 73 selectively covering and uncovering the openings 71.

The electrocauterizing blade 70 is connected electrically to a metal contact 76 in the wall of the tubular body 67. The tubular body 67 fits in supporting sleeve 43 with its metal contact 76 making connection with contact 46. Probe 66 is therefore removably supported in sleeve 43 of holder 41 and may be disposed of without throwing away the control switches 47 and 48. Electrocauterizing blade 70 is connected to electric lead 15 through contacts 76 and 46, and switches 47 and 48 which connect cutting and coagualating or cauterizing frequencies, respectively, from electric lead 15 and generator 11.

While this invention has been shown fully and completely with special emphasis on certain preferred embodiments, it should be understood that within the scope of the appended claims the invention may be practiced otherwise than as specifically described herein.

We claim:

1. An electrosurgical apparatus comprising an electrosurgical generator means having circuit means for producing a cutting current and a coagulation current, a cutting and coagulation probe energized by said generator means having a handle portion and probe element, on/off switch means controlling energization of said probe element, and switch means for switching said probe element between said cutting current and said coagulation current, including
   a holder member removably supporting said probe and having an electric socket means therein,
   said probe comprising a hollow tubular member having a body portion removably fitting said holder member and having a nose portion,
   said probe element comprising an electrocutting and electrocoagulation element secured in and having one end extending outward from the end of said nose portion and the other end positioned inside said tubular member, and
   said probe being removably supported in said holder member and having an electric connector positioned in the wall of said tubular member for contact with said holder member socket means to complete an electric connection to said probe element, and
   an electric connector connecting said probe element to said circuit means.

2. An electrosurgical apparatus according to claim 1 in which said hollow tubular member has an opening at one end adapted for connection by hollow tubing to a source of vacuum, and a side opening adjacent to said one end, said hollow tubular member body portion removably fitting said holder member has a tapered nose portion, an electrocutting and electrocoagulation element secured in and having one end extending outward from the end of said nose portion and the other end positioned inside said tubular member, said nose portion having a plurality of openings adjacent to the tapered surface thereof adapted to withdraw smoke from a surgical area being cut and cauterized by means of a vacuum connected to said tubular member open end, and means for selectively controlling the application of vacuum through said nose portion openings.

3. An electrosurgical apparatus according to claim 2 in which said means for selectively controlling the application of vacuum through said nose portion openings comprises said tubular member side opening and the selective opening and closing thereof.

4. An electrosurgical apparatus according to claim 2 in which said means for selectively controlling the application of vacuum through said nose portion openings comprises said tubular member side opening and the selective opening and closing thereof, and means for selectively covering and uncovering said nose portion openings.

5. an electrosurgical apparatus according to claim 2 in which said tubular member opposite end portion is smaller in outside diameter than said one end portion and the tapered nose portion commences its taper from said smaller diameter.

6. An electrosurgical apparatus according to claim 5 further including a tubular sleeve member supported for longitudinal movement on said smaller diameter portion.

7. An electrosurgical apparatus according to claim 6 in which said sleeve member is imperforate and has an inside diameter permitting sliding movement on said tubular member smaller diameter portion between a retracted and an extended position, and the inside diameter of said sleeve member and tapered surface of said nose portion cooperating when said sleeve member is moved to an extended position to provide a passage for directing flow of smoke and gases from a coagulation site through said nose portion openings and said tubular member when vacuum is applied thereto.

8. An electrosurgical apparatus according to claim 2 in which said tubular member and said nose portion are separate molded plastic pieces, said nose portion fitting inside the other end of said tubular member, and further including a tubular sleeve member supported for longitudinal movement on said nose portion, said sleeve member being inperforate and having an inside diameter permitting sliding movement on said nose portion between a retracted position against said other end of said tubular member and an extended position, and the inside diameter of said sleeve member and tapered surface of said nose portion cooperating when said sleeve member is moved to an extended position to provide a passage for directing flow of smoke and gases from a cauterizing site through said nose portion openings and said tubular member when vacuum is applied thereto.

9. An electrosurgical apparatus according to claim 1 in which said switch means for switching said probe element between said cutting current and said coagulation current is in said holder member.

10. An electrosurgical apparatus according to claim 1 in which said switch means for switching said probe element between said cutting current and said coagulation current is in said holder member, and said on/off switch means is a pedal operated switch connected to said generator means.

11. An electrosurgical apparatus according to claim 1 in which said on/off switch means is in said holder member.

12. An electrosurgical apparatus according to claim 1 in which said on/off switch means is in said holder member, and said switch means for switching said probe element between said cutting current and said coagulation current is a pedal operated switch connected to said circuit means.

13. An electrosurgical apparatus according to claim 1 in which said holder member comprises a body portion having a switch therein and a sleeve portion removably receiving and supporting said probe, and said sleeve having an inner surface with a metal contact thereon comprising said socket means, said probe having a metal contact on its outer surface positioned for contact with said socket means metal contact.

14. An electrosurgical apparatus according to claim 1 in which said holder member comprises a body portion having a switch therein for switching said probe element between said cutting current and said coagulation current and a sleeve portion removably receiving and supporting said probe, and said sleeve having an inner surface with a metal contact thereon comprising said socket means, said probe having a metal contact on its outer surface positioned for contact with said socket means metal contact.

15. An electrosurgical apparatus according to claim 1 in which said holder member comprises a body portion having an on/off switch therein and a sleeve portion removably receiving and supporting said probe, and said sleeve having an inner surface with a metal contact thereon comprising said socket means, said probe having a metal contact on its outer surface positioned for contact with said socked means metal contact.

16. A probe assembly for an electrosurgical apparatus comprising an electrosurgical generator means having circuit means for producing a cutting current and a coagulation current, a cutting and coagulation probe energized by said generator means having a handle portion and a probe element, on/off switch means controlling energization of said probe element, and switch means for switching said probe element between said cutting current and said coagulation current, said probe assembly comprising a probe element, a holder member removably supporting said probe element and having an electric socket means therein, said probe element comprising a hollow tubular member having a body portion removably fitting said holder member and having a nose portion with an electrocutting and electrocoagulation element secured in and having one end extending outward from the end of said nose portion and the other end positioned inside said tubular member, and said probe element being removably supported in said holder member and having a first electric connector positioned in the wall of said tubular member for contact with said holder member socket means to complete an electric connection to said probe element, and a second electric connector connecting said probe element to said first electric connector.

17. A probe assembly according to claim 16 in which said probe element hollow tubular member has an opening at one end for connection by hollow tubing to a source of vacuum, and a side opening adjacent to said one end, said hollow tubular member nose portion is tapered, said nose portion having a plurality of openings adjacent to the tapered portion thereof adapted to withdraw smoke from a surgical area being cut and cauterized by means of a vacuum connected to said tubular member open end, means for selectively controlling the application of vacuum through said nose portion openings.

18. A probe assembly according to claim 17 in which said means for selectively controlling the application of vacuum through said nose portion openings comprises said tubular member side opening and the selective opening and closing thereof.

19. A probe assembly according to claim 17 in which said means for selectively controlling the application of vacuum through said nose portion openings comprises said tubular member side opening and the selective opening and closing thereof, and means for selectively covering and uncovering said nose portion openings.

20. A probe assembly according to claim 17 in which said tubular member opposite end portion is smaller in outside diameter than said one end portion and the tapered nose portion commences its taper from said smaller diameter.

21. A probe assembly according to claim 20 further including a tubular sleeve member supported for longitudinal movement on said smaller diameter portion.

22. A probe assembly according to claim 21 in which said sleeve member is imperforate and has an inside diameter permitting sliding movement on said tubular member smaller diameter portion between a retracted and an extended posiition, and the inside diameter of said sleeve member and tapered surface of said nose portion cooperating when said sleeve member is moved to an extended position to provide a passage for directing flow of smoke and gases from a coagulation site through said nose portion openings and said tubular member when vacuum is applied thereto.

23. A probe assembly according to claim 17 in which said tubular member and said nose portion are separate molded plastic pieces, said nose portion fitting inside the other end of said tubular member, and further including a tubular sleeve member supported for longitudinal movement on said nose portion, said sleeve member being imperforate and having an inside diameter permitting sliding movement on said nose portion between a retracted position against said other end of said tubular member and an extended position, and the inside diameter of said sleeve member and tapered surface of said nose portion cooperating when said sleeve member is moved to an extended position to provide a passage for directing flow of smoke and gases from a cauterizing site through said nose portion openings and said tubular member when vacuum is applied thereto.

24. A probe assembly according to claim 16 in which said switch means for switching said probe element between said cutting current and said coagulation current is in said holder member.

25. A probe assembly according to claim 16 in which said on/off switch means is in said holder member.

26. A probe assembly according to claim 16 in which said holder member comprises a body portion having a switch therein and a sleeve portion removably receiving and supporting said probe, and said sleeve having an inner surface with a metal contact thereon comprising said socket means, said probe having a metal contact on its outer surface positioned for contact with said socket means metal contact.

27. A probe assembly according to claim 16 in which said holder member comprises a body portion having a switch therein for switching said probe element between said cutting current and said coagulation current and a sleeve portion removably receiving and supporting said probe, and said sleeve having an inner surface with a metal contact thereon comprising said socket means, said probe having a metal contact on its outer surface positioned for contact with said socket means metal contact.

28. A probe assembly according to claim 16 in which said holder member comprises a body portion having an on/off switch therein and a sleeve portion removably receiving and supporting said probe, and said sleeve having an inner surface with a metal contact thereon comprising said socket means, said probe having a metal contact on its outer surface positioned for contact with said socket means metal contact.

29. An electrosurgical probe element for use with a hollow holder having an electric socket means comprising a peripheral electric connector strip in the inner surface thereof and associated wiring for connection to a source of cutting and coagulation current comprising a hollow tubular member having a body portion and a nose portion, an electrocutting and electrocoagulation element secured in and having one end extending outward from the end of said nose portion and the other end positioned inside said tubular member, and an electric connector positioned in the wall of said tubular member in the outer surface thereof for contacting said electric means.

30. An electrosurgical probe element according to claim 29 in which
    said probe element comprises a hollow tubular member having an opening at one end adapted for connection by hollow tubing to a source of vacuum, and a side opening adjacent to said one end,
    said hollow tubular member having a body portion removably fitting said holder member and having, at the opposite end, a tapered nose portion,
    an electrocutting and electrocoagulation element secured in and having one end extending outward from the end of said nose portion and the other end positioned inside said tubular member,
    said nose portion having a plurality of openings adjacent to the tapered surface thereof adapted to withdraw smoke from a surgical area being cut and cauterized by means of a vacuum connected to said tubular member open end,
    means for selectively controlling the application of vacuum through said nose portion openings.

* * * * *